(12) United States Patent  
Wong

(10) Patent No.: US 8,294,899 B2
(45) Date of Patent: Oct. 23, 2012

(54) MAPPING CONCENTRATIONS OF AIRBORNE MATTER

(75) Inventor: Colin Irvin Wong, Burnaby (CA)

(73) Assignee: Golder Associates Ltd., Burnaby (CA)

( * ) Notice: Subject to any disclaimer, the term of this patent is extended or adjusted under 35 U.S.C. 154(b) by 0 days.

(21) Appl. No.: 13/379,811

(22) PCT Filed: Oct. 6, 2010

(86) PCT No.: PCT/CA2010/001614
§ 371 (c)(1),
(2), (4) Date: Dec. 21, 2011

(87) PCT Pub. No.: WO2011/041908
PCT Pub. Date: Apr. 14, 2011

(65) Prior Publication Data
US 2012/0092649 A1    Apr. 19, 2012

(30) Foreign Application Priority Data

Oct. 6, 2009 (CA) .................................. 2681681
Oct. 5, 2010 (CA) .................................. 2715677

(51) Int. Cl.
*G01N 21/00* (2006.01)
*G01N 31/00* (2006.01)
(52) U.S. Cl. ............. 356/437; 356/438; 356/72; 702/23; 702/24; 250/338.5; 250/339.13
(58) Field of Classification Search .................. 356/437, 356/438, 72; 250/339.13, 338.5, 573, 574; 702/23, 24
See application file for complete search history.

(56) References Cited

U.S. PATENT DOCUMENTS

| | | | |
|---|---|---|---|
| 4,135,092 A | 1/1979 | Milly | 250/343 |
| 4,204,121 A | 5/1980 | Milly | 250/343 |
| 5,521,883 A | 5/1996 | Fage | 367/90 |
| 5,604,299 A | 2/1997 | Cobb | 73/32.02 |

(Continued)

FOREIGN PATENT DOCUMENTS

CA    2219335    11/1997
(Continued)

OTHER PUBLICATIONS

International Search Report & Written Opinion for PCT/CA2010/001614, Jan. 25, 2011, pp. 1-8.
Office Action for CA 2,715,677 dated Feb. 1, 2011, pp. 1-3.
Notice of Allowance with Allowed claims issued on Jul. 12, 2011 for CA Pat. Application No. 2,715,677, pp. 1-4.
Response to Written Opinion, for Application No. PCT/CA2010/001614, filed Aug. 4, 2011, pp. 1-9.
Babilotte, A., et al., Field intercomparison of methods to measure fugitive methane emissions on landfills. Proceedings Sardinia 2009, 12th International Waste Management and Landfill Symposium S. Margherita de Pula Cagliari, Italy Oct. 5-9, 2009. (6 pages).

(Continued)

*Primary Examiner* — Layla Lauchman
(74) *Attorney, Agent, or Firm* — Ballard Spahr LLP

(57) ABSTRACT

A method of mapping concentrations of airborne matter from an emission source of interest in an emission plume is provided. The method involves measuring airborne matter at one or more than one identified locations using an optical sensing instrument (OSI) operatively connected with one or more than one matter samplers and mounted on a vehicle. The one or more than one airborne matter samplers are passed through an airspace to be sampled, and one or more concentration measurements are obtained. Geographic positions and altitude values for each of the one or more identified locations are established, and a point concentration measurement for the airborne matter for each identified location determined. The concentration measurements are mapped relative to the geographic position and altitude values for each of the one or more identified locations to obtain an airborne matter concentration distribution map in one or more measurement surfaces through a cross-section or profile of the emission plume. The method further comprises a step of determining a representative wind velocity distribution at one or more measurement surfaces and calculating the mass flow rate of airborne matter across the measurement surface in mass per unit time.

20 Claims, 9 Drawing Sheets

U.S. PATENT DOCUMENTS

| | | | | |
|---|---|---|---|---|
| 5,748,325 | A | 5/1998 | Tulip | 356/437 |
| 6,493,086 | B1 | 12/2002 | McAndrew | 356/437 |
| 6,542,242 | B1 | 4/2003 | Yost | 356/450 |
| 6,750,467 | B2 | 6/2004 | Tulip | 250/221 |
| 6,822,742 | B1 | 11/2004 | Kalayeh | 356/437 |
| 6,864,983 | B2 | 3/2005 | Galle | 356/432 |
| 6,995,846 | B2 | 2/2006 | Kalayeh | 356/437 |
| 7,312,452 | B2 | 12/2007 | Klingenberg | 250/339.13 |
| 7,375,814 | B2 | 5/2008 | Reichardt | 356/437 |
| 7,523,638 | B2 | 4/2009 | Princes | 73/1.06 |
| 8,010,300 | B1 | 8/2011 | Stearns | 702/24 |
| 2008/0195329 | A1 | 8/2008 | Prince | 702/32 |
| 2010/0091267 | A1 | 4/2010 | Wong | 702/22 |
| 2011/0122397 | A1 | 5/2011 | Wong | 702/22 |

FOREIGN PATENT DOCUMENTS

| | | |
|---|---|---|
| CA | 2550156 | 7/2005 |
| CA | 2675173 | 7/2008 |
| CA | 2655279 | 5/2009 |
| EP | 1972922 | 9/2008 |
| WO | WO 2011/041908 | 4/2011 |

OTHER PUBLICATIONS

Babilotte, A., et al., "Fugitive methane emissions from landfills: A field comparison of five methods on a French landfill", Global Waste Management Symposium, Colorado, Sep. 7-10, 2008. (15 pages).

Babilotte, A., et al., "Fugitive Methane Emissions from Landfills: Field Comparison of Five Methods on a French Landfill." Journal of Environmental Engineering 136(8): 777-784, 2010.

Brown, D.M., "Remote sensing techniques in the infrared region of the electromagnetic spectrum", MSc Thesis, The Pennsylvania State University, Department of Electrical Engineering, May 2005. (53 pages).

Chambers, A., "Optical Measurement Technology for Fugitive Emissions from Upstream Oil and Gas Facilities", report prepared by Alberta Research Council Inc., Dec. 15, 2004. (79 pages).

Chambers, A., et al, "DIAL Measurements of Fugitive Emissions from Natural Gas Plants and the Comparison with Emission Factor Estimates", 15th International Emission Inventory Conference, New Orleans, May 15-18, 2006. (11 pages).

Czepiel, et al, "Landfill methane emissions measured by enclosure and atmospheric tracer methods", Journal of Geophysical Research, 101(D11): 16711-16719, 1996.

Denmead, O.T., "Approaches to measuring fluxes of methan and nitrous oxide between landscapes and the atmosphere", Plant Soil 309: 5-24, 2008.

Desjardins, R.L., et al., "Evaluation of a micrometeorological mass balance method employing an open-path laser for measuring methan emissions", Atmospheric Environment 38: 6855-6866, 2004.

Frisch, L., "Fugitive VOC-emissions measured at Oil Refineries in the Province of Vastra Gotaland in South West Sweden—a success story", development and results 1986-2001 commissioned by the County Administration of Västra Götaland. (32 pages).

Gregory, R and Armstrong, K. Review of Landfill Surface Emissions Monitoring DEFRA Report, Jun. 11, 2007 (74 pages)).

Gregory, R.G. and Armstrong, K.S., "Review of Landfill Surface Emissions Monitoring", presented at Global Waste Management Symposium, Colorado, USA, Sep. 7-10, 2008. (9 pages).

Griffith, D., et al., "Methane Emissions from Free-Ranging Cattle: Comparison of Tracer and Integrated Horizontal Flux Techniques", Journal of Environmental Quality, 37(2): 582-591, 2008.

Hashmonay et al., "Innovative Approach for Estimating Fugitive Gaseous Fluxes Using Computed Tomography and Remote Optical Sensing Techniques", Journal of the Air & Waste Management Association, 49: 966-972, 1999.

Hensen, A., & Scharff, H., "Methane Emission Estimates from Landfills Obtained with Dynamic Plume Measurements", Water, Air and Soil Pollution: Focus, 1(5-6): 455-464, 2001.

Huitric, R.L., and Kong, D., "Measuring Landfill Gas Collection Efficiency Using Surface Methane Concentrations", SWANA 29th Annual LFG Symposium, St. Petersburg, Florida, Mar. 27-30, 2006. (11 pages).

Lamb, B., et al., "Development of Atmospheric Tracer Methods to Measure Methane Emissions from Natural Gas Facilities and Urban Areas", Environmental Science & Technology, 29: 1468-1479, 1995.

Laubach, J., and Kelliher, F., "Methane emissions from dairy cows: Comparing open-path laser measurements to profile-based techniques", Agricultural and Forest Meteorology, 135: 340-345, 2005.

Lenz, Dawn et al., "Flight Testing of an Advanced Airborne Natural Gas Leak Detection System", Final Report, ITT Industries Space Systems LLC, Rochester, NY, Oct. 2005. [http://www.netl.doe.gov/technologies/oil-gas/publications/td/41877_final.PDF] . (84 pages).

Mays et al "Aircraft-Based Measurements of the Carbon Footprint of Indianapolis" from the Oct. 15, 2009 issue of Environmental Science & Technology. (4 pages).

Milly, G.H., "The Vertical Grid Assessment of Air Pollution Sources", Int. J. Air Wat. Poll., 8: 291-295, 1964.

Mount, G. et al, "DOAS Measurement of Atmospheric Ammonia Emissions at a Dairy", 10th Annual Emission Inventory Conference, EPA, 2001. (15 pages).

Oonk, H., "Literature Review: Methane from Landfills. Methods to Quantify Generation, Oxidation and Emission", Report for Sustainable Landfill Foundation, Apr. 2010. (75 pages).

Scharff, H., "Landfill Gas Production and Emission on Former Landfill", Interreg IIIC report (on the internet), Oct. 2005. (16 pages).

Thoma, E., et al, "Development of EPA OTM 10 for Landfill Applications Interim Report 2", Global Waste Management Symposium, Colorado, USA, Sep. 7-10, 2008. (13 pages).

Thornton, E. & Bowmar, N., "The Application of a Laser Based Open-Path Spectrometer for the Measurement of Fugitive Emissions and Process Control", A & WM Association Conference, Raleigh, North Carolina, Oct. 28, 1999. (9 pages).

Trégourés, A., et al., "Comparison of seven methods for measuring methane flux at a municipal solid waste landfill site", Waste Management & Research, 17: 453-458, 1999.

United States Environmental Protection Agency, "Evaluation of Fugitive Emissions Using Ground-based Optical Remote Sensing Technology", EPA 600/R-07/032, Feb. 2007. [http://www.epa.gov/nrmrl/pubs/600r07032/600r07032.pdf]. (111 pages).

United States Environmental Protection Agency, "Optical Remote Sensing for Emission Characterization from Non-point Sources", Jun. 14, 2006. (44 pages).

Van den Kroonenberg, A. and Bange, J. "Turbulent flux calculation in the polar stable boundary layer: Multiresolution flux decomposition and wavelet analysis" Journal of Geophysical Research 112:, DO06112, doi:10.1029/2006JD007819, 2007. (12 pages).

Varma, R.M., 2004, Optical Remote Sensing for Air Quality Monitoring, Agra, India, Dec. 6-8, 2004. (14 pages).

Weibring, P., et al, "Remote monitoring of industrial emissions by combination of lidar and plume velocity measurements", Applied Physics B Lasers and Optics, 66: 383-388, 1998.

Whiteman, D.N. et al., "Raman Airborne Spectroscopic Lidar (RASL)—Final Report", Ralcon Development Labs, Sep. 30, 2002. [http://ramanlidar.gsfc.nasa.gov/instruments/raman%20airborne%20spectroscopic%20lidar/rasl-final-report.pdf]. (42 pages).

Office Action issued Feb. 7, 2011 for U.S. Appl. No. 12/575,854, filed Oct. 8, 2009 (Inventor—Colin I. Wong) (17 pages).

Office Action issued Jan. 6, 2012 for U.S. Appl. No. 12/964,149, filed Dec. 9, 2010 (Inventor—Colin I. Wong) (29 pages).

Notice of Allowance issued Jul. 2, 2011 for Canadian Patent Application No. 2,715,677, filed Oct. 5, 2010 (Inventor—Colin Irvin Wong // Applicant—Colin Irvin Wong) (1 page).

Office Action issued Feb. 1, 2011 for Canadian Patent Application No. 2,715,677, filed Oct. 5, 2010 (Inventor—Colin Irvin Wong // Applicant—Colin Irvin Wong) (3 pages).

Office Action issued Jul. 2, 2010 for Canadian Patent Application No. 2,681,681, which was filed on Oct. 6, 2009 (Inventor—Colin Irvin Wong // Applicant—Golder Associates Ltd.) (9 pages).

International Search Report and Written Opinion issued Jan. 25, 2011 for PCT/CA2010/001614 filed on Oct. 6, 2010 and published as WO 2011/041908 on Apr. 14, 2011 (Inventor—Colin Irvin Wong // Applicant—Golder Associates Ltd.) (9 pages).

Office Action issued on Jun. 3, 2009 for Canadian Patent Application No. 2,655,279, which was filed on Mar. 10, 2009 (Inventor—Colin Irvin Wong // Applicant—Colin Irvin Wong) (3 pages).

Office Action issued on May 19, 2010 for Canadian Patent Application No. 2,655,279, which was filed on Mar. 10, 2009 (Inventor—Colin Irvin Wong // Applicant—Colin Irvin Wong) (4 pages).

Office Action issued Oct. 7, 2009 for Canadian Patent Application No. 2,655,279, which was filed on Mar. 10, 2009 (Inventor—Colin Irvin Wong // Applicant—Colin Irvin Wong) (3 pages).

"Regional ozone and urban plumes in the southeastern United States: Birmingham, a case study", Journal of Geophysical Research, Sep. 20, 1995, vol. 100, No. D9, pp. 18823-18834.

MAPPING CONCENTRATIONS OF AIRBORNE MATTER

CROSS REFERENCE TO RELATED APPLICATIONS

The present application is a National Phase Application of International Application No. PCT/CA2010/001614, filed Oct. 6, 2010, which claims priority to Canadian Patent Applications No. 2,681,681, filed Oct. 6, 2009, and No. 2,715,677, filed Oct. 5, 2010, which applications are incorporated herein fully by this reference.

FIELD OF INVENTION

The present invention relates to methods for mapping airborne concentrations of airborne matter in an emission plume.

BACKGROUND OF THE INVENTION

Fugitive emissions result from releases of airborne matter to the atmosphere from diffuse sources, which can include landfills, reservoirs, effluent ponds, mines, natural deposits, or even a collection of point-sources such as cities, industrial plants, or a herd of animals. Fugitive emissions can also include emissions from point sources, such as smokestacks, flares, wells, exhaust tubes, leaks and vent pipes, that have been released to the atmosphere. The airborne matters can be greenhouse gases, gaseous organic compounds, polluting gases, or particulate matter. The atmospheric volume within which the airborne matters exist is referred to as a plume. The flux is the mass flow rate per unit area. The mass flow rate is the flow rate of the airborne matter through an imaginary surface, for example downwind of an emission source, in mass per unit time. The emission discharge rate is the mass flow rate discharged by an emission source to the atmosphere in mass per unit time. The mass flow rate, if measured downwind of an emission source, and the emission discharge rate, are the same if the background concentration of airborne matter is zero and attenuation is accounted for.

Denmead (2008, Plant Soil 309:5-24) describes various approaches to measuring fluxes of methane and other subject gases between landscapes and the atmosphere. In particular, it is disclosed that mass balance methods are useful for defined source areas in the tens to thousands of square meters. Conventional micrometeorological techniques may also be employed for source areas of a similar size, but may necessitate sampling periods in the order of several minutes to hours under some conditions, or for some subject gases.

When assessing fugitive emissions from large sources such as a large landfill using current techniques, the emissions are monitored at or near the surface level, or at the edges of the landfill. Such an arrangement may involve the placement (permanently or temporarily) of a plurality of sensors or sampling devices; this placement may be limited by access to the site. Spot surface measurements may under or over estimate the emission by not detecting points with significant emissions, or by detecting a localized region of high concentration (e.g. where the gas is trapped and concentrated in a pocket or depression). Estimates and extrapolations, while useful for monitoring and modeling emission plume movement, may not be suitable in some situations where defined values are desired. Another method is to use a tracer gas and measure sample concentrations downwind of the emission source. However, tracer techniques cannot be used to determine the variation of airborne matter concentration near a diffuse source, and the tracer release pattern should mimic the emission flux pattern from the emission source.

U.S. Pat. No. 6,542,242 discloses a method for mapping of airborne matter using path-integrated optical remote sensing (ORS) with a non-overlapping variable path beam length geometry (Radial Plume Mapping). Radial Plume Mapping uses optical remote sensing instruments to obtain path-integrated data, that is processed reiteratively using a cumulative distribution function to provide a map of the concentration of airborne matters. The assumed radial concentration pattern is determined based on an assumed cumulative density function. The method, in a vertical configuration, requires a ground-based, stable vertical structure on which to mount reflectors.

U.S. Pat. No. 4,135,092 and U.S. Pat. No. 4,204,121 teach mass balance methods using either a number of totalizing samplers mounted on a vertical pole or line, an aircraft flying through the plume at various elevations collecting total samples at several height intervals, or vertically spaced infrared radiation transmitters on a mast opposite another mast with a matching series of infra-red receptors. Sampling can be made upwind of the source area to evaluate the contribution of incoming pollution to the apparent fugitive emission rate. However, it does not teach how to determine the concentration distribution of airborne matter within the plume or account for a natural background concentration of a pollutant in the atmosphere.

Canadian patent application 2,655,279 provides a method for measurement of fugitive emission mass flow rate using an optical remote sensing instrument mounted either on an airborne platform (for ground-based targets), or with the instrument mounted on the ground and the targets mounted on an airborne platform.

Milly (1964, Int. J. Air Wat. Poll 8:291-295) describes a method for mapping of contaminant concentrations in the air using ground-based fixed masts, and samplers at various heights on each mast. The airspace to be mapped is limited by the height of the mast and the area covered by the samplers, and may not be practical for large emission plumes spanning several hectares and/or of significant height.

U.S. Pat. No. 6,750,467 and Canadian patent 2,219,335 describe a vehicle-mounted apparatus (a "GasFinder", Boreal Laser Inc.) which allows for rapid point measurements of airborne matter concentrations. Thornton and Bowmar (A&WM Association Conference, Raleigh N.C. Oct. 28, 1999) also describe the use of the "GasFinder" (Boreal Laser Inc.).

U.S. Pat. No. 6,864,983 teaches the use of a spectrometer for receiving absorption spectra from the sun, from which emission flux can be calculated. The method depends on the availability of direct sunlight and may only be used on sunny days. In addition, the accuracy of the method for some gases is questionable due to the long absorption distance through the atmosphere. For example, the significant background concentration of methane in the atmosphere results in a very large integrated concentration of methane, compared with the contribution of most methane emission plumes.

Mapping of airborne matters can also be carried out using Differential Absorption Laser Detection and Ranging (DIAL). It can be classified as a mass balance method that uses two Nd:YAG (neodymium-doped yttrium aluminium garnet; $Nd:Y_3Al_5O_{12}$) lasers. This equipment can map the concentration of airborne matters in the air, from which an emission flux can be calculated (Chambers et al., 15th International Emission Inventory Conference, New Orleans, La., May 2006). In an emission flux measurement application, this equipment is ground based, expensive, heavy and bulky.

U.S. Pat. No. 6,882,742 and U.S. Pat. No. 6,995,846 provide an airborne DIAL, using ND:YLF (neodymium-doped yttrium lithium fluoride; $Nd:YLiF_4$) lasers for detection of natural gas pipeline leaks, providing a path-integrated concentration of methane and ethane. The DIAL instrument described does not map the concentration of airborne matter in the air, and there is no teaching of measuring or quantifying emission flux of the gas leak.

A method to obtain the concentration distribution of airborne matter is needed, where such measurements are obtained without the need for a tracer gas or dispersion modeling, and within a reasonable time frame across the width, depth and length of an emission plume of large area and/or height that may exceed that of ground-based moveable platforms, to provide a map of concentration of the airborne matter through a cross-section or profile of the plume. This map can then be applied to a wind velocity distribution map to obtain the emission discharge rate of airborne matter released by an emission source.

The present invention provides for a method of mapping airborne concentrations of airborne matter in an emission plume using rapid point sampling.

SUMMARY OF THE INVENTION

The present invention relates to a method of mapping concentrations of airborne matter in an emission plume using point sampling. The present invention also provides a method for measuring the emission discharge rate from an emission source in units of mass per unit time.

It is an object of the invention to provide an improved method of mapping concentrations of airborne matter.

The present invention provides a method (A) of mapping airborne concentrations of airborne matter in an emission plume, comprising:
 a) measuring airborne matter at one or more than one identified locations using an optical sensing instrument (OSI) mounted on a vehicle operatively connected with one or more than one matter samplers mounted on the vehicle, by passing the one or more than one matter samplers through an airspace to be sampled and obtaining one or more concentration measurements, a geographic position and an altitude value for each of the one or more identified locations; and
 b) mapping the concentration measurements relative to the geographic position and altitude values for each of the one or more identified locations to obtain an airborne matter concentration distribution map in one or more measurement surfaces through a cross-section or profile of the emission plume.

The present invention also provides a method (B) of obtaining a mass flow rate of airborne matter from an emission source of interest using the method (A) as described above, further comprising the additional steps of:
 c) determining a wind velocity for each identified location in the one or more measurement surfaces to obtain a wind velocity distribution map for each of the one or more measurement surfaces; and
 d) integrating the airborne matter concentration value for each point in the one or more measurement surfaces with the wind velocity for each identified location in the one or more measurement surfaces to obtain the mass flow rate of airborne matter in mass per unit time.

The present invention also provides the method (A) as described above, further comprising a step of correcting for a background concentration of airborne matter or an upwind emission source by determining the background concentration of the airborne matter and subtracting this concentration from the measured concentration of airborne matter at the one or more than one identified locations.

The present invention also provides the method (B) as described above, further comprising a step of correcting for a background concentration of airborne matter or an upwind emission source by correcting the mass flow rate determined in step d) by using the steps of a) to d) to determine the mass flow rate of airborne matter upwind of the emission source of interest.

The present invention provides the method (A) or (B) as described above wherein in the step of measuring (step a), the airborne matter is measured using an optical sensing method selected from: tunable diode laser (TDL) absorption spectroscopy, differential absorption laser detection and ranging (DIAL), open path Fourier transform infrared (OP-FTIR) spectroscopy, differential optical absorption spectroscopy (DOAS) or Raman spectroscopy. The one or more matter samplers includes a measurement cell comprising an air sample and a measurement beam. The optical sensing instrument and measurement cell may be combined into a single unit, such as in a cavity ringdown spectrometer. The wind velocity is obtained with an anemometer or sodar or by differential measurement of vehicle air velocity and vehicle ground velocity. The altitude value is determined using a laser range finder or an altimeter in conjunction with topographic information. The geographic position is determined using a global positioning system, radar, or one or two or more range finder lasers that are set-up to triangulate the position of the airborne platform. The length of the one or more measurement surfaces may be about equal to, or greater than the length of the emission plume, and the height may be about equal to, or greater than the height of the emission plume. The vehicle may pass through an airspace comprising the emission plume along a transverse straight path, or along a curved path, relative to the wind direction. The emission source may be localised or diffuse. The airspace may comprise the emission plume, or a portion of the emission plume.

The vehicle may be an aircraft or a land conveyance vehicle. The aircraft may be an airplane (including ultralights), glider, or helicopter. The one or more matter sampler may comprise a single pass cell, a multipass cell; the matter sampler or the air sample inlet may be fixed to an external surface of the airborne platform, may be within the airborne platform, or towed under or behind the airborne platform on a dragline. The land conveyance vehicle may be self propelled or a trailer pushed or pulled by another vehicle.

The present invention also includes a computer readable memory having recorded thereon statements and instructions for execution by a computer to carry out the method as described above.

The identified locations sampled by the matter sampler and OSI according to the methods described herein may be arranged in a substantially vertical surface that extends from the ground to the upper limit, or beyond of the emission plume. In an x,y,z orientation, the wind direction is substantially along the x axis, with the measurement surface extending in the y and z axes.

Measurement occurs along measurement paths (also termed flight paths if an aircraft is used). Successive vertically spaced sampling runs along the measurement path form a distinct sampling surface (a measurement surface). The measurement paths need not be parallel or straight. The lowermost flight path may approximate the contour of the ground; alternately, it may be independent of the contour of the ground.

The methods described herein allow for obtaining the concentration of airborne matter at a plurality of identified locations within a reasonable time frame and can be used to obtain such concentrations throughout the entire thickness and width of the emission plume and provide a two-dimensional or three-dimensional map of the concentration of airborne matter. The methods can account for variations of wind speed at various heights above the ground and may be applied to emission sources over a large area or height that may extend beyond an above-ground platform or into areas inaccessible, or poorly accessible by ground. The method employs existing airborne matter concentration measurement apparatus for rapidly mapping airborne matter concentrations in the air, and combines this mapping with wind velocity for measuring the emission discharge rate from an emission source. Complex numerical modeling of airborne matter dispersion, or release of a tracer gas is not required.

Methods according to various embodiments of the present invention may be useful for identifying the boundaries, or geographical locations within or surrounding the emission plume where the airborne matter concentration is at or below a selected concentration or flux value. For example, at a landfill site, it may be of interest to determine the location within the measurement surface where the airborne matter concentration is highest. By successive measurement surfaces across the landfill, the emission discharge rate from and location of high emission zones can be identified for increased landfill gas collection.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE DRAWINGS

These and other features of the invention will become more apparent from the following description in which reference is made to the appended drawings wherein.

DETAILED DESCRIPTION

The present invention relates to a method of mapping concentrations of airborne matter in an emission plume using point sampling.

The following description is of a preferred embodiment.

The present invention provides a point measurement method of mapping airborne concentrations of airborne matter in an emission plume using point sampling. The method involves measuring airborne matter at one or more than one identified locations using an optical sensing instrument (OSI) mounted on a vehicle operatively connected with one or more than one matter samplers mounted on the vehicle. The one or more matter samplers are passed along one or more measurement paths through an airspace to be sampled, and one or more concentration measurements are obtained. A geographic position and an altitude value is established for each of the one or more identified locations, and a concentration measurement for the airborne matter for each identified location is then determined. The concentration measurements along the one or more measurement paths are mapped relative to the geographic position and altitude values for each of the one or more identified locations to obtain an airborne matter concentration distribution map in one or more measurement surfaces, or a three-dimensional map of the airborne matter concentration distribution. The measurement surface may be of any shape or orientation, and can be vertical or substantially vertical. For example, the measurement surface may be from about −45 to about +45 degrees (135 degrees), or any amount therebetween from vertical, assuming that vertical is 90 degrees. For example from about 45 to about 135 degrees, or any amount therebetween, assuming that vertical is 90 degrees, for example 45, 50, 55, 60, 65, 70, 75, 80, 90, 95, 100, 105, 110, 115, 120, 125, 130 and 135 degrees or any amount therebetween, from about 80 to about 100 degrees or any amount therebetween, 85 to 95 degrees or any amount therebetween, or from about 87, 90 or 93 degrees.

By “measurement path” it is meant a vehicle path in plan view, along which concentration, location and altitude measurements are obtained. “Sampling runs” are traverses with a vehicle at different elevations along or substantially along the same measurement path.

By “measurement surface” it is meant a virtual surface that comprises a collection of data points (point concentration measurements) obtained along a length and a height, and in some cases a depth, of a measurement path. The data points are obtained at identified locations along the measurement path and include data points obtained following multiple sampling runs carried out at different elevations or heights along the measurement path. Since the locations of the data points (point concentration measurements) are known, the data points can be mapped to define the measurement surface. The measurement surface may be planar (two dimensional)

comprising data points obtained along a length and a height, or curved (three dimensional), comprising data points obtained along a length, a height and a depth. For example, which is not to be considered limiting, three sampling runs, each carried out substantially along a similar measurement path, may be used to collect data (point concentration measurements) to produce a measurement surface. Each sampling run obtains a plurality of data points along a measurement path at a defined height. The location of the data points is determined, and the combined data points from each sampling run at three different heights are plotted to produce the measurement surface. It is to be understood that due to practical constraints, the measurement path may vary between each sampling run. Since the geographical position and altitude for each data point along a measurement path is determined, the resulting location of each data point may be mapped to produce a measurement surface. Multiple sample runs may be obtained that may not align along a single measurement path. These data may be retained to produce a three-dimensional measurement surface. Alternatively, the data points obtained from these multiple sample runs may be projected in the wind direction onto a representative measurement surface. The representative measurement surface may be used for example, for calculation or presentation purposes, as required.

Figure 6:
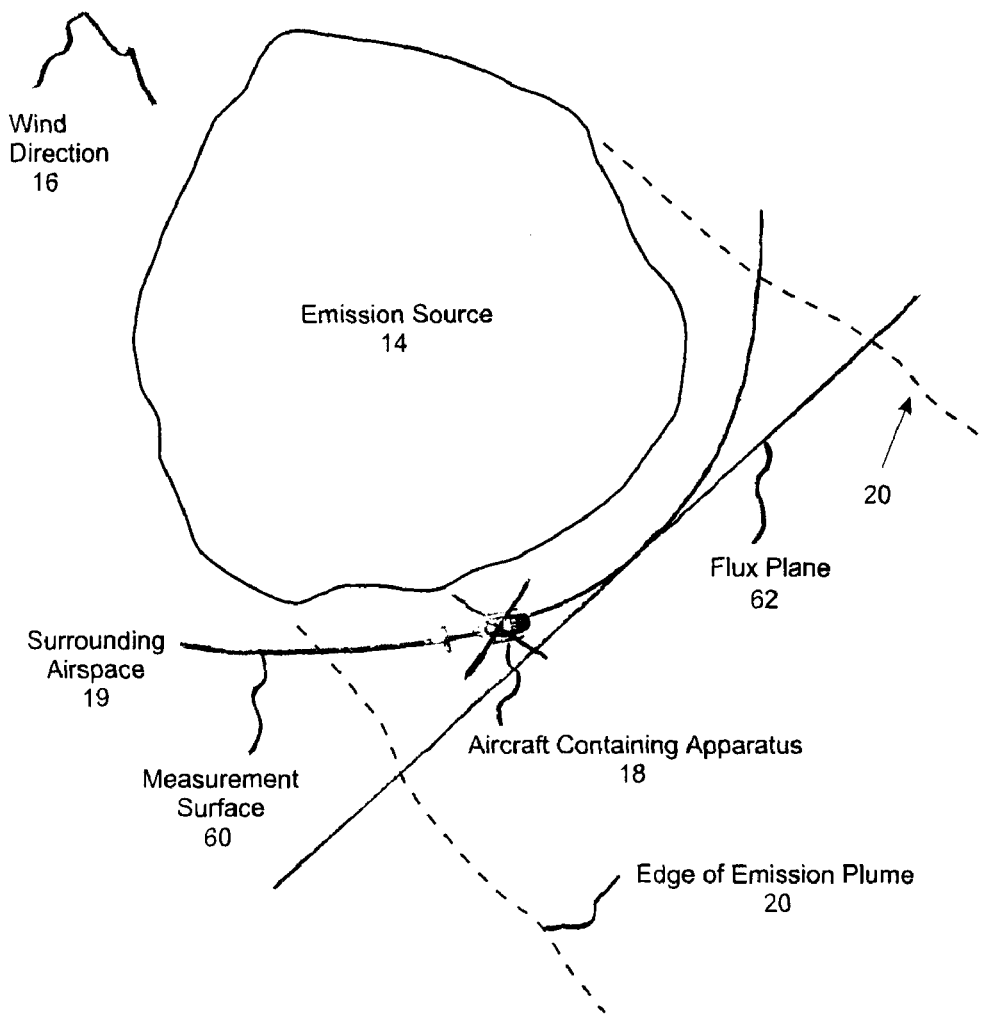
FIG. 6 shows a plan view of the mode shown in FIG. 1, showing an emission source, an aircraft, a flight (measurement) path near the edge of the emission source, and the flux plane which is shown to be perpendicular to the wind direction.

For ease of visualization and data presentation, each measurement surface may be projected in the wind direction onto a flux plane (see FIG. 6). The flux plane is the projection of the measurement surface point values onto a plane that is perpendicular to the wind direction.

The method may further comprise determining or estimating wind velocity for each identified location in the one or more measurement surfaces to obtain a wind velocity distribution profile for each of the one or more measurement surfaces.

The present invention also provides a method of obtaining a mass flow rate of airborne matter from an emission source of interest. The method involves measuring airborne matter at one or more than one identified locations along one or more measurement paths, using an optical sensing instrument (OSI) mounted on a vehicle operatively connected with one or more than one matter samplers mounted external to the vehicle, by passing the one or more than one airborne matter samplers through an airspace to be sampled along a measurement path, and obtaining one or more concentration measurements, a geographic position, and an altitude value for each of the one or more identified locations. The concentration measurement may be mapped relative to the geographic position and altitude values for each of the one or more identified locations to obtain a measurement surface or a three-dimensional map of the airborne matter concentration distribution. A wind velocity may be determined or estimated for each location in the one or more measurement surfaces to obtain a wind velocity distribution profile for each of the one or more measurement surfaces. For ease of visualization and presentation, the values of the measurement surface may be projected in the wind direction onto a flux plane that is transverse to the wind direction (see FIG. 6). For computational ease, the flux plane may be perpendicular to the wind direction. The airborne matter concentration value for each point in the one or more flux planes, or measurement surfaces, is integrated with the wind velocity value for the point in the one or more flux planes, or measurement surfaces, to obtain the mass flow rate of airborne matter in mass per unit time across the measurement surface.

Examples of airborne matter from an emission source of interest include, but are not limited to compounds, molecules, one or more than one gas of a single species or a mixture of two or more gasses for example but not limited to greenhouse gasses for example but not limited to carbon dioxide, methane, nitrous oxide, and the like, gaseous organic compounds for example combustible gasses, natural gas, methane, ethane, propane, or emissions from petrochemical plants, polluting gasses for example, sulphur dioxide, ammonia, ozone, vehicle emissions, emissions from landfills, industrial emissions, radioactive emissions, toxic emissions, particulate material and the like. Airborne matter may also be referred to as a subject gas.

Figure 1:
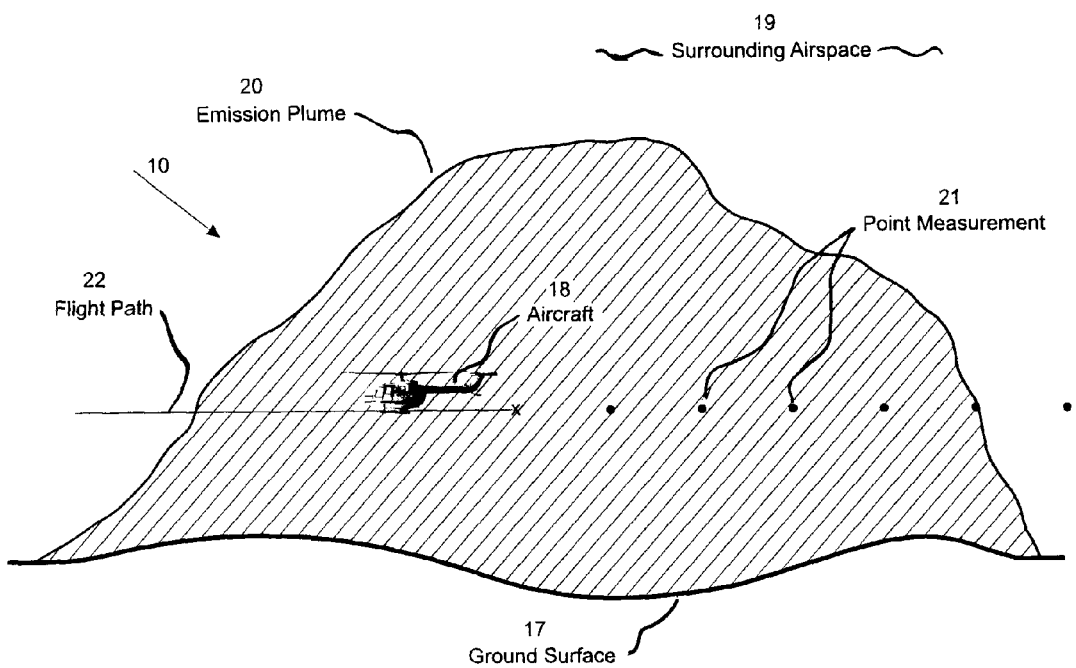
FIG. 1 shows a cross-section view of an example of the invention, showing a vehicle (in this case an aircraft) having a flight (measurement) path above the ground surface and through a cross-section of an emission plume.
Figure 2:
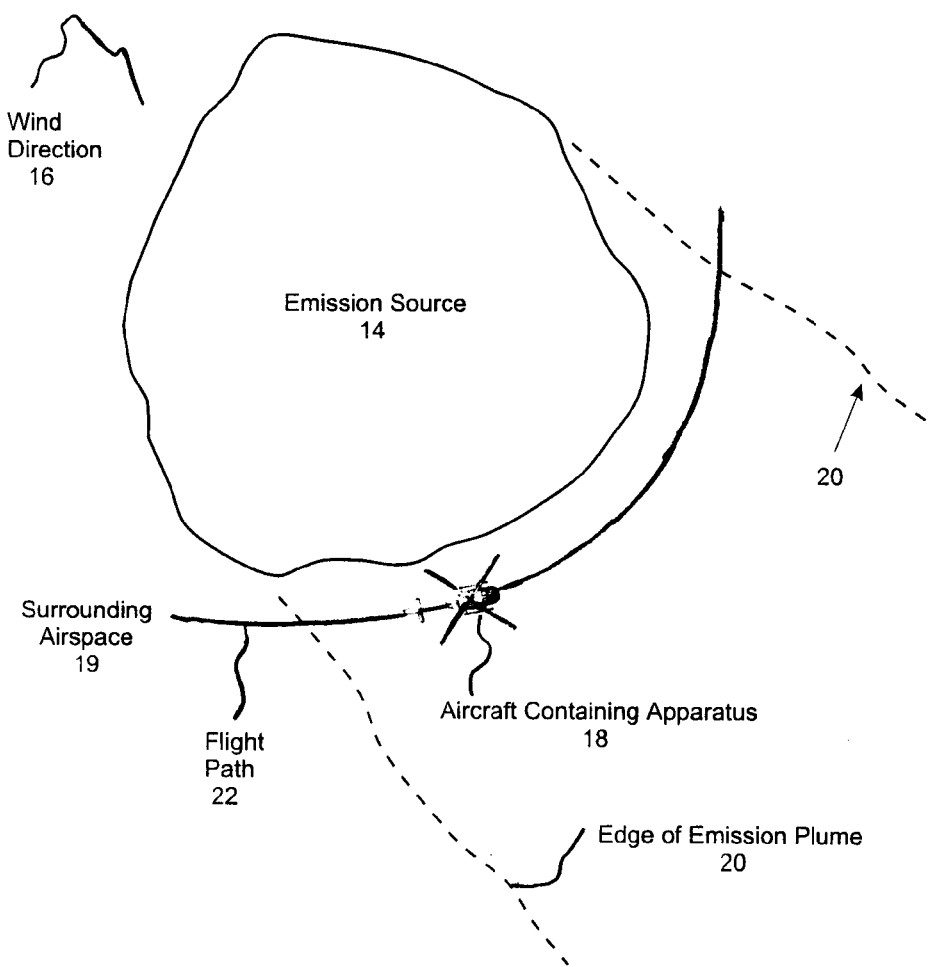
FIG. 2 shows a plan view of the mode shown in FIG. 1, showing an emission source, an aircraft and a flight (measurement) path through the emission plume near the edge of the emission source.

With reference to FIGS. 1 and 2, there is shown a non-limiting example of the present invention. A vehicle, in this case an aircraft 18, is shown, however, a land-based vehicle or trailer may also be used. An OSI and one or more matter samplers are mounted on the vehicle, that passes through an emission plume 20 caused by an emission source 14 within the surrounding airspace 19, to obtain one or more point concentration measurements at one or more identified locations (21). In this example, the measurement path is a flight path, 22, and that defines the location of a measurement surface. Measurements obtained at different elevations and from multiple sampling runs along the flight path (22), are combined to produce a measurement surface. The measurement surface may be contained within the emission plume, or may extend beyond one or more boundaries or edges of the emission plume. The measurement surface may be oriented as close to the emission source of interest as practical. There may be more than one measurement surface. The measurement, or flight, path may be straight or curved, it may vary in elevation, and be transverse or parallel to a wind direction 16. A transverse flight path may be from about 175 to about 5 degrees from the wind direction, or any amount therebetween (e.g. not parallel to the wind direction), for example 5, 10, 20, 30, 40, 50, 60, 70, 80, 90, 100, 120, 130, 140, 150, 160, 175 degrees from the wind direction, or any amount therebetween. Measurements obtained along curved measurement paths and that are used to define a curved measurement surface, will produce a three-dimensional map of the airborne matter.

If the one or more measurement surfaces are parallel or substantially parallel to the wind direction, then the map of concentrations would be that of a profile of a plume. While a single profile may be used to obtain a mass flow rate for a fugitive emission, a single profile may not be an ideal measurement surface for this purpose. Preferably, a transverse or curved measurement surface is used to obtain a mass flow rate as described herein.

The emission plume may be of any size or shape, ranging from a few meters in height to several hundred, and from a few square meters in area to several hectares, to several square kilometers. For example, the emission source may be a single leak in a pipeline, or a cluster of leaks close together (described as a point source), and the fugitive emission forming a plume from the point source (moving with the ambient wind velocity). Alternatively, the emission source may be diffuse, for example from a landfill with a soil cover. The fugitive emission forms a plume from the multiple point sources, which may not be individually discernable given the rate of emission and/or size of the plume. An increase in airborne matter concentration immediately downwind of a particular point may be indicative of a point source that is the primary source of fugitive emissions, while a more diffuse concentration profile may be indicative of a plurality of point sources scattered over the area.

Preferably, the flight path 22 extends beyond the edges of the emission plume 20. The flight path 22 defines a line of a measurement surface along which one or more measurements may be obtained at one or more identified locations.

Figure 3:
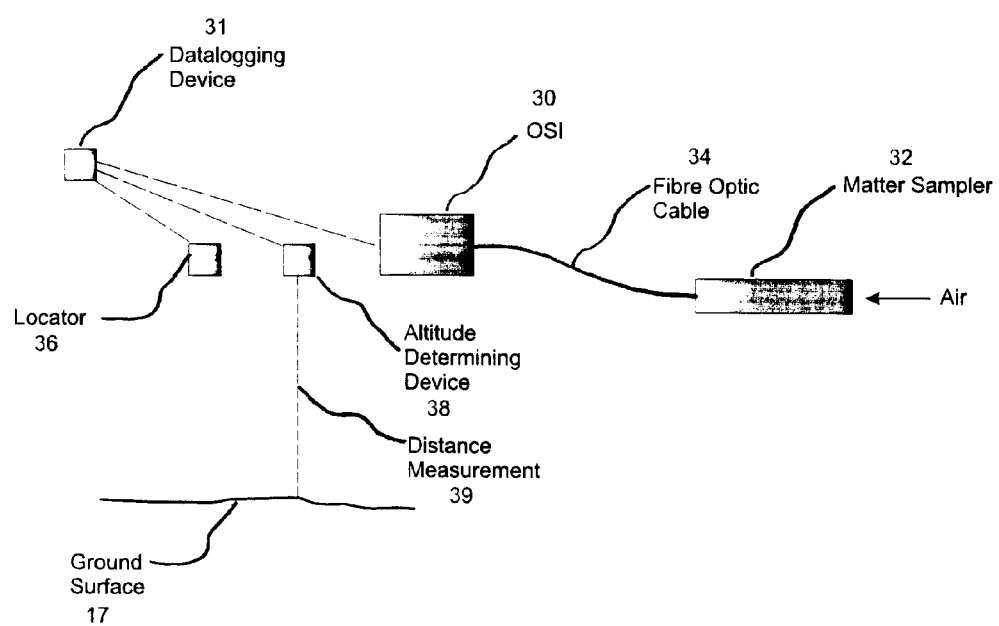
FIG. 3 shows a schematic diagram of air from an airspace flowing into a matter sampler, operatively connected to an optical sensing instrument (OSI) by a fibre optic cable. A datalogging apparatus collects data received from the OSI, a location device and a distance measurement device (to determine the distance between the vehicle housing the above apparatus and the ground).

Referring to FIG. 3, a non-limiting schematic illustration of components mounted on the vehicle is shown. Optical sensing instrumentation (OSI) 30 is operatively connected by a fiber optic cable 34 to one or more matter samplers 32, and is also connected to a datalogging device 31. A locator 36 and an altitude-determining device 38 are also operatively connected to the datalogging device 31. The OSI and matter sampler may be a single unit, such as in a cavity ring-down spectrometer, and may not need a fiber optic cable.

The locator 36 provides geographic position information, for example latitude and longitude or other coordinates, of the vehicle, thus providing latitude and longitude or other coordinates for the identified location where airborne matter is measured. Examples of locators include a global positioning system (GPS) or radar, or range finder lasers. The range finder lasers would be set-up to point at and then triangulate the position of the vehicle. An altitude determining device provides altitude for the vehicle, thus providing altitude, or distance 39 above the ground surface 17, for the identified location where airborne matter is measured. Examples of altitude determining devices include a laser range finder, radar, sonar, a fixed measure (e.g. a tape measure) or an altimeter in conjunction with topographic information. The altimeter may be a GPS; in this embodiment, the locator 36 and altitude determining device 38 are in a single unit. Typically the locator 36, altitude determining device 38, OSI 30, matter sampler 32 and fiber optic cable 34 are associated with the same vehicle.

Figure 4A:
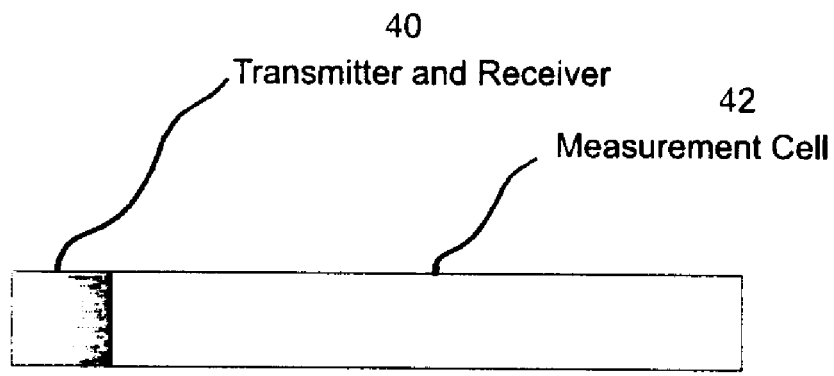
FIG. 4 shows a schematic diagram of a matter sampler, comprising a measurement cell and a transmitter and receiver at a first end (A) or comprising a measurement cell having a transmitter at a first end and a receiver at a second end (B).
Figure 4B:
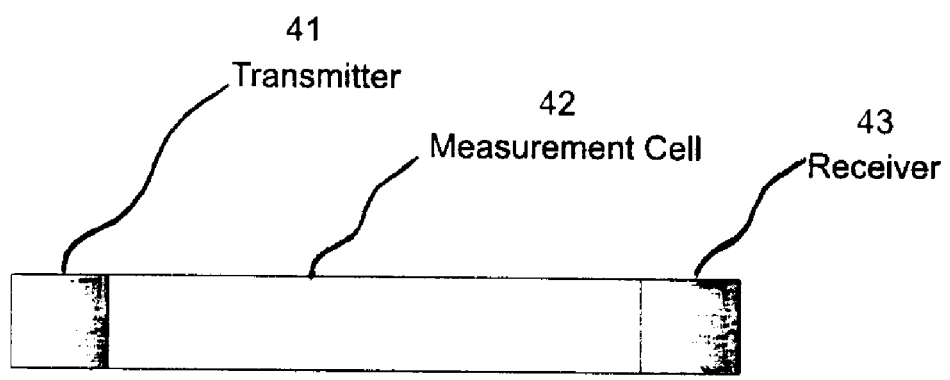

Referring to FIGS. 4A and 4B, the matter sampler includes a transmitter, a receiver, and a measurement cell. The transmitter and receiver may be located at a first end 40 of a measurement cell 42; alternately, the transmitter 41 may be at a first end of the measurement cell and the receiver at a second end 43. A plurality of matter samplers may be operatively connected to one OSI. Alternatively, each matter sampler may be operatively connected to a separate OSI. Inside each matter sampler, the beam of the OSI is directed into the measurement cell and the concentration of the airborne matter in the matter sampler is recorded by the OSI at discrete and, preferably, frequent intervals (preferably between 1 and 10 Hertz, for example 1, 2, 3, 4, 5, 6, 7, 8, 9 or 10 Hertz). The measurement cell includes an airspace for the measurement beam. The measurement cell may be a multipath cell. Non limiting examples of multipath cells include an optical cavity, Herriott cell, a White cell, a cavity ring-down spectrometer, or a variable length Herriot-type multipass cell as described in EP1972922.

Air from the exterior of the vehicle flows into the measurement cell of the matter sampler, and the concentration of the airborne matter is recorded. The matter sampler may be mounted to an external surface of the vehicle; alternately air may enter an air sample intake and be funneled, drawn, or pumped to one or more matter samplers housed within, or on the vehicle. The air entering the measurement cell may be representative of the airspace at the identified location at the time of measurement. Alternatively, there may be a slight time delay (typically 2 seconds or less) in the air entering the measurement cell compared to the airspace at the identified location, and an appropriate correction to the location of the measurement is made. As the one or more matter samplers pass through the various zones (concentration, wind velocity, temperature, etc.) within the plume, the concentration of the airborne matter within the plume is recorded as a point measurement or discrete concentration at the identified location. The measurement of the airborne matter concentration by the OSI within the measurement cell at the time of measurement, at an identified location, is considered to be a point measurement. At the time of each measurement, the location and height above ground surface of the air sample intake, that is part of the matter sampler, is recorded, thus uniquely describing each of the identified locations.

At least two sampling runs or traverses, with the air sample intake of the one or more matter sampler, at different heights above the ground surface are obtained. The runs may be straight or curved. Greater detail and an increased accuracy of the cross-section or profile of the emission plume may be obtained if measurements are taken at, at least, three altitudes, one of which is near the top of the plume. However, additional sampling runs may also be obtained, for example 2, 3, 4, 5, 6, 7, 8, 9, 10 or more sampling runs at different heights along a measurement path. Increased accuracy may be realized by having the sampling runs in a common vertical, or substantially vertical, surface (a measurement surface).

Figure 5:
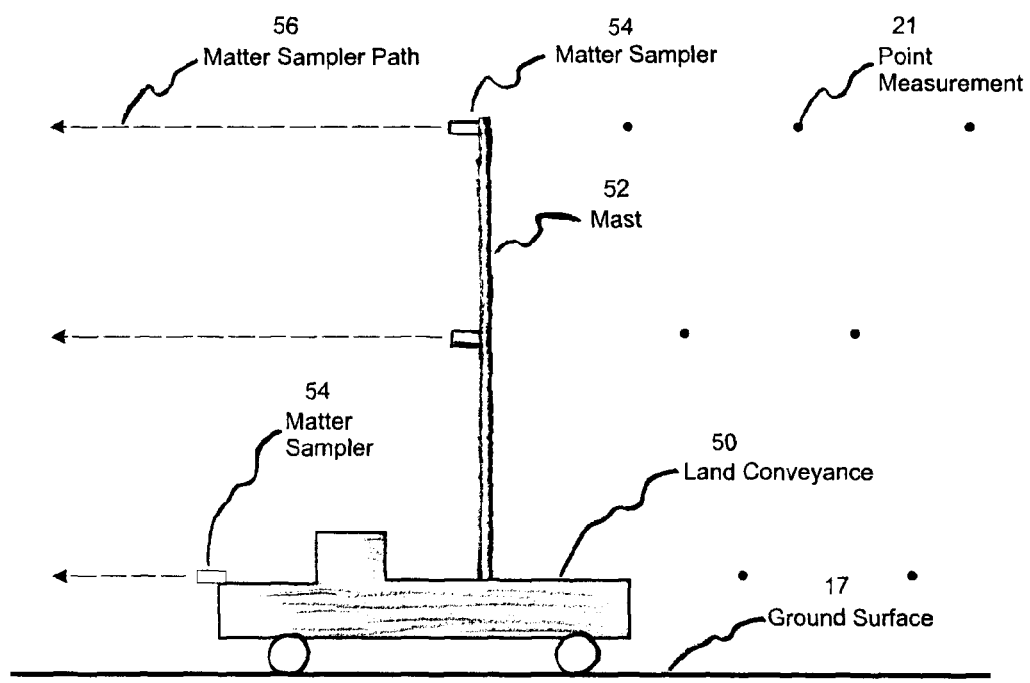
FIG. 5 shows a profile view of a second mode, showing a mobile, ground based land conveyance comprising a plurality of matter samplers mounted at defined heights above the ground surface. The path of the matter samplers is indicated in the dashed lines.

It may be useful, or preferred (for reasons of safety, expediency and/or accuracy, for example) to obtain measurements near the ground surface with a land conveyance, such as that illustrated in FIG. 5. The land conveyance may be a car, truck, cart, trailer, or other ground-based vehicle. For ease of reference, the path of the land conveyance may also be referred to as a "measurement path" or a 'flight path'. Alternatively, one or more matter samplers may be moved along a 'flight path' close to the ground by attaching the matter samplers (or their air sample intakes) to the distal end of an aircraft based tether or dragline. The land conveyance may be equipped with a mast or balloon with one or more matter samplers (or their air sample intakes) fixed at specified heights (see FIG. 5). Similar to using an aircraft, the land conveyance comprises the apparatus exemplified in FIG. 3, travels across the ground along a measurement path, obtaining measurements of airborne matter concentration at identified locations within a measurement surface.

The point measurement concentration data obtained for the identified locations may be displayed as a plot of concentration measurements in the measurement surface.

A top-view schematic of an emission plume downwind from an emission source is illustrated in FIG. 2. This fugitive emission plume comprises varying concentrations across the cross-section of the plume. A vehicle, in this case an aircraft, comprising an OSI, operatively connected with one or more matter samplers may be used to obtain concentration measurements at various identified locations along a measurement path providing a three-dimensional grid, or measurement surface, of concentration values. The concentration values of the measurement surface may be projected in the wind direction onto a flux plane that is transverse to the wind direction (see FIG. 6). A flux plane may be from about 175 to about 5 degrees from the wind direction, or any amount therebetween (e.g. not parallel to the wind direction), for example 5, 10, 20, 30, 40, 50, 60, 70, 80, 90, 100, 120, 130, 140, 150, 160, 175 degrees from the wind direction, or any amount therebetween. For example, the flux plane may be perpendicular to the wind direction, and vertical in orientation. FIG. 6 illustrates the relationship between the measurement surface 60 and the flux plane 62 when the flux plane is perpendicular to the wind direction.

Figure 7:
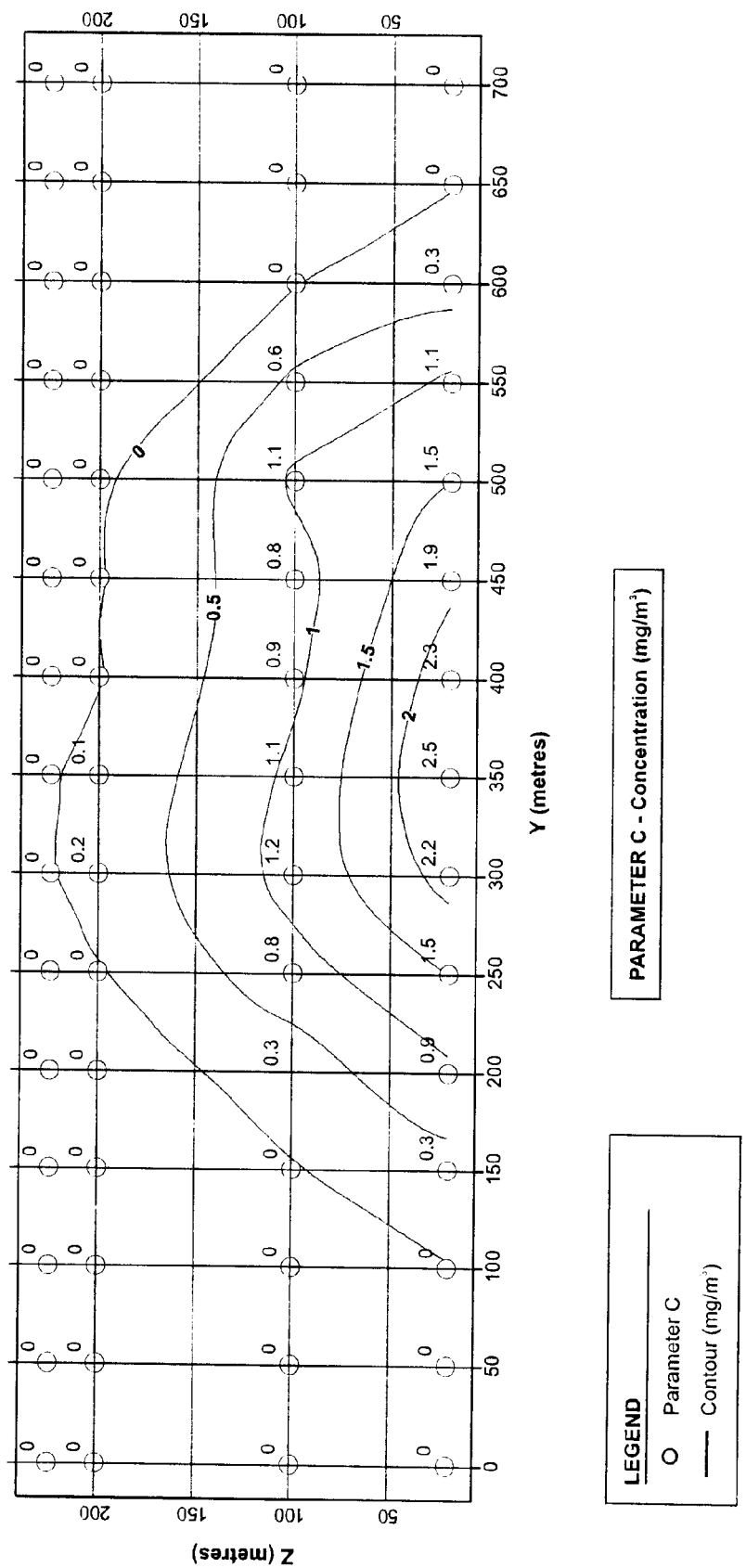
FIG. 7 shows a flux plane plot with point measurements and contour line plots at 0.5 mg/cu·m intervals of concentrations of airborne matter as Parameter C.

In the flux plane plot illustrated in FIG. 7, the identified locations are close to, or at ground level (e.g. within 10-20 meters of the ground), at 100 meters above the ground, at 200 meters above the ground, and at 250 meters above the ground. Identified locations were about 50 meters apart across the ground. The contour lines of concentration of airborne matter, Parameter C, (in this case, methane) in units of milligrams per cubic meter are shown, after subtracting the background concentration.

In order to calculate the airborne matter mass flow rate at the identified measurement surface, at least one wind velocity value for the measurement surface is obtained. For example, at least one wind velocity value may be obtained for each measurement path. One or more devices to measure the wind velocity may be required. It may be useful, and it may provide increased accuracy, if wind velocity is determined at, or near to, the measurement surface. Wind velocity may be measured by, for example, an anemometer. If two or more anemometers are installed at the same location but at different heights, then the wind velocity may be a function of the height above ground surface. Alternatively, empirical relationships can be used to determine the change in wind velocity with height above ground. If two or more anemometers are installed at different locations, then the wind velocity can be a function of both the length along the measurement surface and the height.

A method for measuring wind velocity at heights greater than a ground-based anemometer is to fly an aircraft, equipped with an air speed measuring device, at a constant air speed, preferably, directly with or against the wind. The difference between the air speed, measured with the air speed measuring device, and the ground speed, determined by the locator (36, FIG. 3) such as a GPS, is the wind speed.

The wind velocity data may be displayed as a plot in a plane perpendicular to the wind direction. This plane is referred to as the wind plane. The plot of wind velocity would show the variation of wind speed across the wind plane, such as that exemplified in FIG. 8 as Parameter W.

Figure 8:
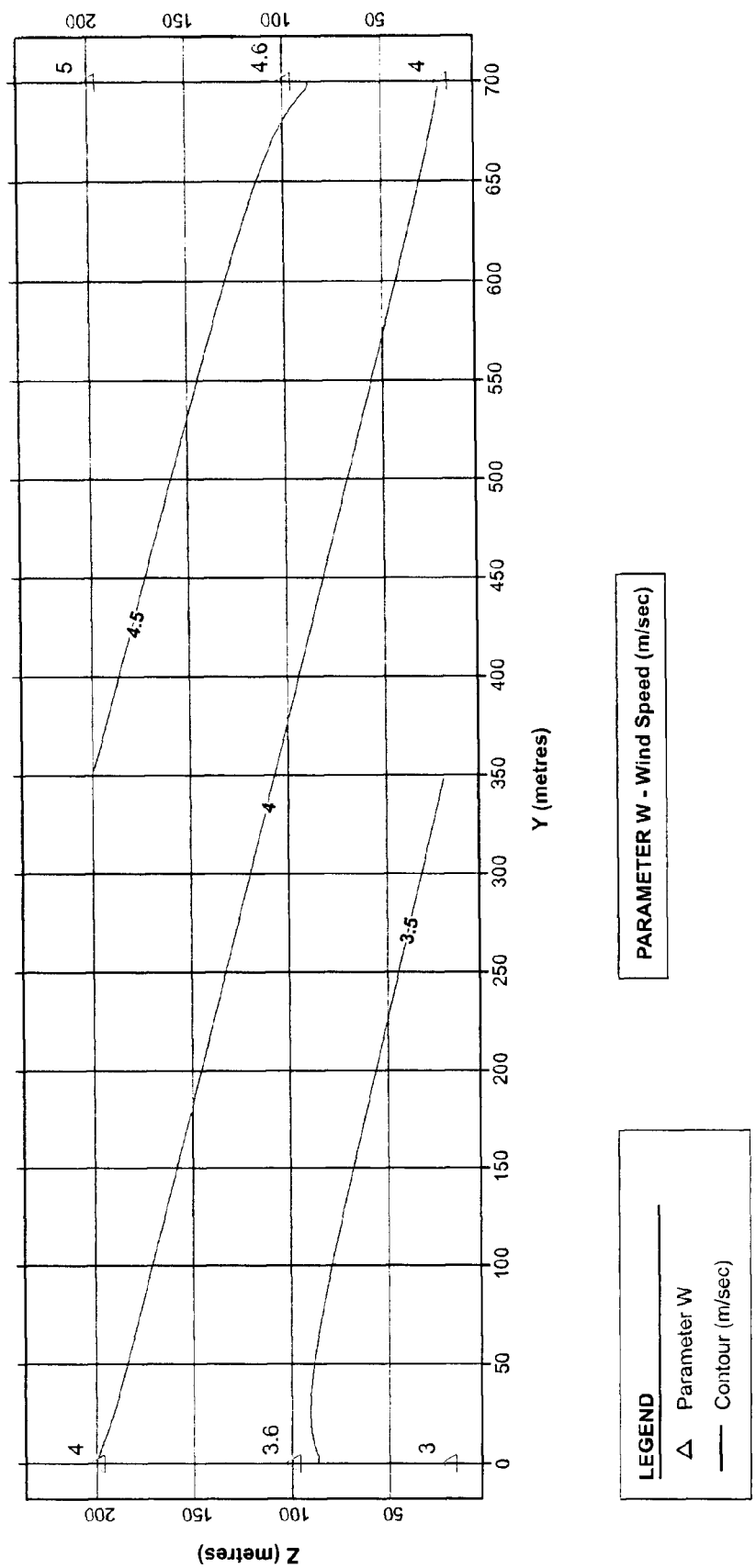
FIG. 8 shows wind speed at three elevations above the ground, and contour lines at 0.5 m/second intervals as Parameter W.

In the wind speed plot (map) shown in FIG. 8, wind velocity was determined flanking the identified locations, close to, or at ground level (e.g. within 10-20 meters of the ground), at 100 meters above the ground, and at 200 meters above the ground. The contours of wind speed in meters per second across the wind plane is shown in FIG. 8.

Alternatively, the wind speed plot may be simplified by averaging the wind speed over the measurement surface (thus the wind speed map would be a single value).

Figure 9:
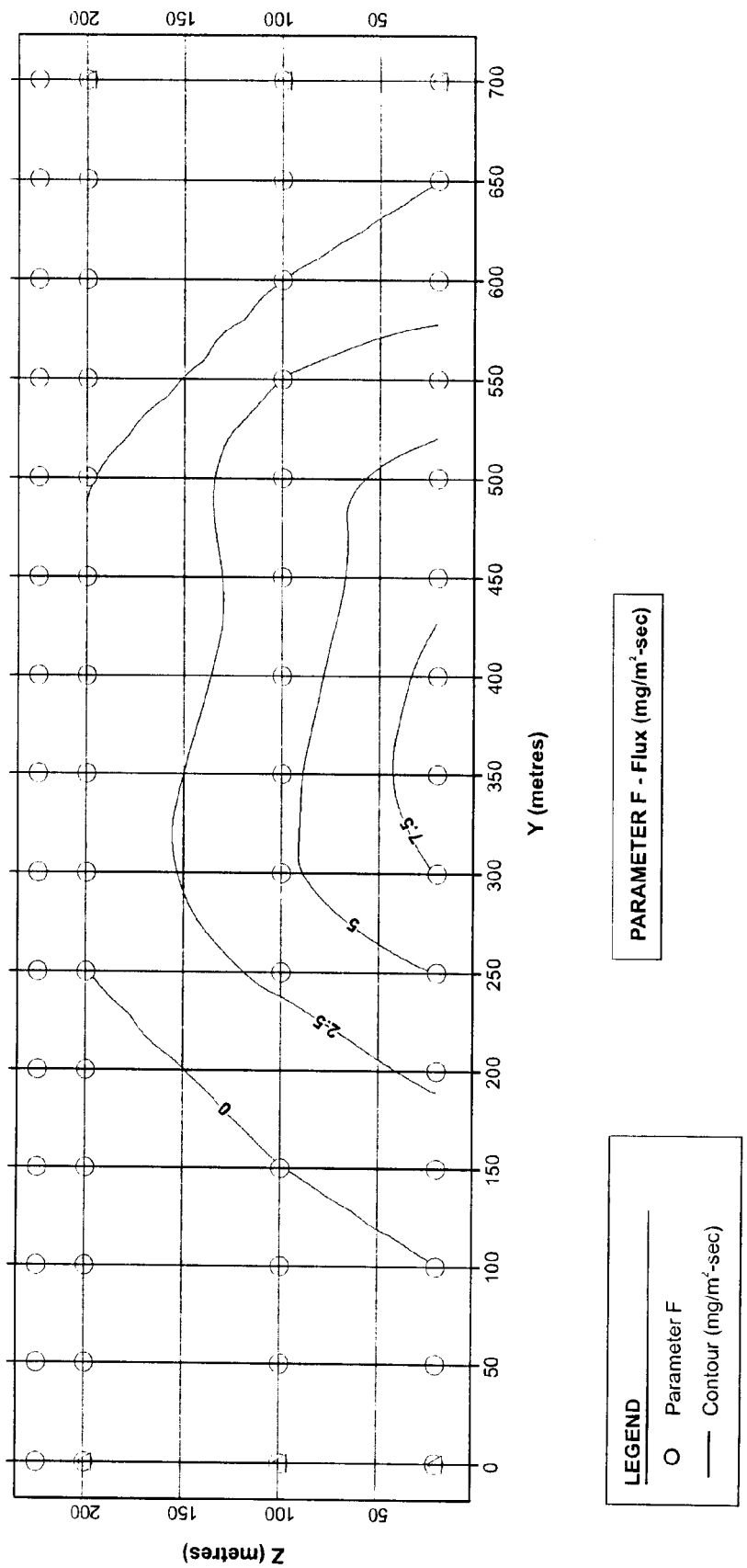
FIG. 9 shows contour line plots at 2.5 mg/m2-sec intervals of concentration multiplied by wind speed, illustrating the variation of flux of airborne matter through the measurement surface, as Parameter F.

The airborne concentration data of the measurement surface or flux plane (FIG. 7) and the wind velocity data for each identified location (FIG. 8) may be integrated to provide Parameter F, as shown in the plot exemplified in FIG. 9, illustrating emission flux contours in milligrams per meter squared-second. Any conventional mathematical technique may be used to perform such an integration. Alternatively, a computer program, such as Surfer (available from Golden Software) and ArcView (available from ESRI, Redlands Calif.) can be used for the contouring and integration computations. The contour areas shown in FIG. 9, of Parameter F, may then be integrated to obtain the mass flow rate of airborne matter across the measurement surface in mass per unit time.

The matter samplers are positioned upon a vehicle so that the air sampled is representative of the air at the identified location. For example, if the vehicle is a helicopter, 'propeller wash' from the rotor blades may disrupt the airflow and result in sampling of airspace that is above the helicopter. To facilitate accurate data collection, the helicopter may thus be flown at a sufficient speed to negate the effect of the propeller wash; alternatively, the matter sampler may be attached to a dragline and towed behind and below the helicopter, out of the way of the propeller wash. The appropriate speed, or range of speeds, suitable will be dependent on the environmental conditions (e.g. local wind speed), and the characteristics of the helicopter (size, rotor type and/or speed, and the like). The results of available wind tunnel studies, empirical testing, or air flow modelling may be useful in determining the minimum speed of flight. As an illustrative example only, a speed of about 50 to about 100 km/h across the ground, or greater, may be suitable for initial considerations, for example 50, 60, 70, 80, 90 or 100 km/h, or any amount therebetween. Regardless of the nature of the aircraft, rapid measurements of the airborne matter are preferable to obtain accurate point concentration data with respect to position.

Two or more matter samplers may also be mounted on the vehicle. For example, one matter sampler, or its air sample intake, may be fixed to an external surface of an aircraft, and a second or subsequent matter samplers, or its air sample intake, attached to a dragline or tether and towed below and/or behind the aircraft. Such an arrangement would effectively provide for the equivalent of two sampling runs with a single pass of the aircraft.

To account for a background concentration of airborne material, it may be useful to measure the concentration of airborne matter at one or more identified locations outside the boundary of the emission plume (for example, upwind of the emission source). This background concentration value may be subtracted from the concentration measurements of the identified locations within or surrounding the emission plume.

For emission sources that cover a large area, there may be attenuation of the airborne matter from a local point of emission until the airborne matter reaches the measurement surface. Attenuation mechanisms could include diffusion, dilution, absorption, adsorption, exchange, reaction, degradation, or other processes. Any number of available techniques known in the art may be applied to correct for such attenuation, depending on the mechanism involved. For example as a non-limiting illustration, airborne matter at the fringes of a large plume may become diluted to such an extent that this portion of the airborne matter becomes indistinguishable from background concentrations and may thus not be detected at the measurement surface at the downwind edge of the emission source. Dispersion modelling or empirical analysis of other measurement surfaces downwind of the measurement surface closest to the emission source may be used to correct for this attenuation. If the potential for attenuation is insignificant, then a correction for attenuation is not required.

Existing methods do not provide for mapping of fugitive emission concentrations of airborne matter within large plumes greater than about 10 m in height and do not allow for identification of the lateral and vertical extent or highest concentration areas of an emission plume. Conventional point sampling equipment does exist, however it may be unsuitable for point sampling using a rapidly moving vehicle, as it may not provide a fast enough response (in the case of a gas chromatograph) or with sufficient accuracy or resolution (e.g. flame ionization detection) to accurately map contaminant concentrations.

Operation and Equipment

The concentration of airborne matter in an emission plume may be mapped as follows:
 i) determine the site to be profiled;
 ii) determine the airborne matter, gas, material, or a combination thereof to be measured;
 iii) determine a measurement path;
 iv) select an OSI with a suitable electromagnetic wavelength or wavelengths (for example, if multiple species of airborne material are to be measured);
 v) connect the OSI to one or more matter samplers, with each matter sampler including a measurement cell;

vi) using the OSI and matter samplers, obtain point concentrations of airborne matter across a length, height, and optionally a depth, of a measurement path; and vii) record the location and distance from ground surface of the air sample intake of each matter sampler at the time of each measurement to create a measurement surface.

The fugitive emission mass flow rate of airborne matter across a measurement surface that is transverse to the wind direction may be obtained by additionally viii) determine the wind velocity at one or more locations and use this information to develop a two dimensional map (wind plane) of wind velocity across the measurement surface;

ix) project the concentration values of the measurement surface (obtained in vii) in the direction of the wind onto a flux plane; and x) using the values of concentration in the flux plane together with the wind plane information, calculate the emission mass flow rate of the airborne matter across the measurement surface in mass per unit time.

The apparatus for carrying out a method of the invention may comprise a vehicle having mounted thereon an OSI operatively connected with one or more than one matter samplers. The apparatus may further comprises a locator (36, FIG. 3) to locate the vehicle (and thus the identified location of the point measurement) by at least geographic position (e.g. latitude, longitude) and an altitude value (38, FIG. 3) or position.

Optical sensing instrument (OSI) apparatus employed in step (v) above, and for the methods, apparatus and systems as described herein refers to an optical measurement apparatus whose measurement beam can be aimed or focused in a particular direction. The OSI is equipped with a transmitter and receiver of the optical or electromagnetic energy and a space for such energy to transmit through the sample of airborne matter in air.

The OSI, with the matter sampler, provides data output in the form of a measurement in units of mass of airborne matter per unit volume or in units of volume per volume.

The OSI may comprise tunable diode laser (TDL) instruments, for example manufactured by Boreal Laser Inc., differential absorption laser detection and ranging (DIAL) instruments for example as used by ITT ANGEL Service, open path Fourier transform infrared (OP-FTIR) spectroscopy instruments for example manufactured by Edo Corporation, or differential optical absorption spectroscopy (DOAS) instruments for example manufactured by Opsis Inc. Other methods, such as Raman spectroscopy, or any other open path measurement technique as would be known to one of skill in the art, may also comprise the OSI.

The measurement beam produced by the OSI may be provided by, for example but not limited to, one or more lasers of one or more wavelengths, or a light or electromagnetic radiation source (EMR) of one or more wavelengths, including at least one wavelength that is absorbed by a gas or particulate of interest. The measurement beam is of a brightness that meets the requirements of the methods taught herein. For example such light or electromagnetic radiation (EMR) sources could include a laser, a tunable diode laser, a laser followed by a frequency conversion device, an incandescent light, an EMR source passing through an appropriate filter, or an LED source. The light or EMR source is capable of emitting at a single-wavelength or multiple wavelengths as required. In addition, the beam generated by the light, EMR, or laser is intended to include wavelengths that are efficiently propagated across the measurement path, and includes electromagnetic radiation in the ultraviolet, visible, near infrared, or infrared portions of the spectra, as appropriate. If desired, alternate sources, for example thermal, ultrasound, radio waves, microwaves, or X-rays may also be used for a measurement beam, as required.

The OSI further comprises one or more than one detector to receive a portion of the measurement beam that is either transmitted directly from the transmitter, through the air sample within the measurement cell, and to the receiver or detector, or transmitted from the transmitter, reflected one or more than once through the air sample within the measurement cell and to the receiver (such as would occur within a multipass cell). The detectors may include multiple detectors, or an array of detectors and the detector may be removed from the unit housing the measurement beam source. The data so obtained is stored by a data logging apparatus or 'datalogger', such as computer readable memory, or processed using an algorithm with a central processing unit (CPU).

The OSI is operatively connected to one or more matter samplers. The one or more matter samplers may be directly connected to the OSI (i.e. the light or EMR shines through the measurement cell of the matter sampler to the detector) or the one or more matter samplers may be connected via fibre optic cable to the OSI. The measurement cell provides for a measurement beam length to achieve the desired accuracy. It may comprise a single mirror to reflect the energy from the transmitter to the detector, an open airspace between the transmitter and receiver, or an assemblage of mirrors, known in the art such as a Herriot cell, that lengthen the measurement beam length while maintaining the apparatus at a compact size. For example in some embodiments, if an OSI's resolution is 1 ppm-m, the desired measurement accuracy is 0.1 ppm, and there is space within the vehicle, or the equipment housing for a straight beam length of only 1 m, then a multipass cell may be used to extend the effective beam length to 10 m within the 1 m of available room by reflecting the collimated light beam through the air sample multiple times. Thus by selecting a single pass or a multipass cell, the effective beam length may be from about 0.1 meters to several kilometers; for example 0.1, 1.0, 10, 100, 1,000, 10,000 meters or more, or any amount therebetween. The effective beam length required depends on the required resolution of measurement. For example for methane with a background concentration of 1.7 ppm, a resolution of 0.25 ppm or less would be desirable; a measurement beam length of at least 4 m would therefore be desirable if the OSI's resolution is 1 ppm-m. For cavity ringdown spectroscopy, a measurement beam length of several kilometers is desirable.

The one or more than one detector is generally a photon detector, however if appropriate, thermal detectors may also be used. A detector is selected to be compatible with the measurement beam employed. For example, an OSI and detector may be designed to detect methane using the mid to near infrared range (wavelengths of 0.7-8 microns), while determining other airborne matter or subject gas concentration, for example benzene concentration, a detection beam containing wavelengths in the ultraviolet range may be useful (wavelengths of 0.01 to 0.40 microns). Other suitable wavelengths for other airborne matter species will be apparent to those skilled in the relevant art.

The OSI and matter sampler may also be effectively integrated, such as in a cavity ring-down spectrometer. In this case, the multi-pass cell extends the cavity ring-down time to a magnitude that can provide measurements to the accuracy desired.

The apparatus as illustrated schematically in FIG. 3 is mounted within, or fixed to the outside of the vehicle. Alternatively, only the matter sampler is external to the vehicle. In another embodiment, an air sample intake hose that is part of the matter sampler, may extend from the external side of the vehicle to the apparatus mounted in the interior of the vehicle. The apparatus is transported along a measurement path so that point concentrations of airborne matter at identified locations are obtained. At least two, or more sampling runs or traverses of the emission plume by a matter sampler, along the measurement path, at two or more elevations are performed. Where a vehicle includes two or more matter samplers, or their air sample intakes, at two or more altitudes (for example as shown in FIG. 5), a single pass of the vehicle may be sufficient.

The vehicle may be an aircraft or a land conveyance. The aircraft may be an airplane, an ultralight aircraft, a glider, a helicopter or the like, the land conveyance may be a self-propelled vehicle, or a trailer. The position of the vehicle should be controllable by a user to allow for positioning and measurement.

Background concentration of the airborne matter in air is considered to be the concentration of the airborne matter in the atmosphere in the absence of an emission source. The background concentration may be determined by measuring the concentration of airborne matter in the atmosphere in the absence of an emission source. The local background concentration can be obtained with the OSI and a matter sampler, or with any number of available measurement methods known in the art.

If a second emission source exists, or may exist, upwind of the emission source of interest (the 'upwind emission source'), then the mass flow rate from the upwind emission source may also need to be determined so that it may be subtracted from the total mass flow rate downwind of the emission source of interest to obtain the mass discharge rate of the emission source of interest. In examples where the background concentration of the airborne matter is considered to be zero, or substantially zero, the step of adjusting for the background concentration may be omitted.

When a single OSI is used with multiple matter samplers, then one of several available multiplexing techniques may be employed such that a single OSI instrument can monitor the multiple matter samplers at the same time. Techniques that are known in the art, for example but not limited to, wavelength division multiplexing (WDM) and time division multiplexing (TDM) may be used.

One or more wind velocity measurement devices may be used to measure the wind speed and direction at a location or locations that are representative of the wind velocity across the measurement surface. The wind velocity measurement device may be a local measurement instrument, for example an anemometer, or a remote measurement instrument such as sonic detection and ranging (Sodar) instrumentation (see, for example, U.S. Pat. No. 5,521,883). In some embodiments, the wind velocity and OSI data may be recorded and logged in a time-synchronous manner. Alternately, the wind velocity data and OSI data may be recorded independently by the same datalogging device, or by two or more separate datalogging devices, and the recorded data time-stamped to allow for correlation of wind velocity with OSI data at a later point. In some embodiments, more than one wind velocity measurement device may be used. Alternately, the wind measurement data may be input into an emissions dispersion, fluid flow model or wind velocity model to obtain the variation of wind across the measurement surface. Use of a plurality of wind velocity measurement devices may be useful for large emission plumes.

The concentrations of airborne matter and the variation of wind velocity across the measurement surface may be applied to the following equation:

$$M = \int_b^a \int_d^c C(y, z, t) u(y, z, t) \, dy \, dz$$

where M is the mass flow rate of airborne matter in mass per unit time in the x direction, C is the point concentration, x is the wind direction, u is the wind speed in the x direction, y is the horizontal direction that is perpendicular to the wind direction, z is the vertical direction that is perpendicular to the wind direction, t is time, a and b are limits in the z direction and c and d are limits in the y direction. The equation does not have an x variable and thus the construction of a flux plane, while useful for visualization and presentation of the data, is not necessary for the application of the method.

M is also the emission discharge rate from an emission source if the background concentration of airborne matter has already been subtracted from the point concentration data and attenuation has been accounted for, if necessary.

If the wind speed u and concentration C at each point are assumed constant with time, the equation can be rewritten:

$$M = \int_b^a \int_d^c C(y, z) u(y, z) \, dy \, dz$$

Similar equations may be developed if the x-y-z coordinate system is rotated, as may be useful, for example, if the ground surface is sloped.

Mass includes weight, since weight is the product of mass and acceleration due to gravity.

If only a single wind velocity measurement device is employed, then the function u(y,z) becomes u(z) since the wind speed is assumed to be constant in the y direction. An average wind speed can also be assumed such that the wind speed is a constant and not a function of z. However, a more accurate approach is to apply the results of this single wind velocity measurement device to empirical relationships available in the art that relate wind speed to height above ground surface, to obtain u(z).

The concentration measurements, or their projection in the wind direction, may be plotted in y-z space (i.e. in the flux plane), the wind measurements are plotted in y-z space (i.e. the wind plane), and the two maps are integrated to obtain the mass flow rate across the measurement surface in mass per unit time. Alternatively, maps in the physical sense may not be produced. Rather, the maps are digitally stored as data points.

If desired, each point concentration measurement may be multiplied by the wind velocity at the point concentration measurement location (identified location) to obtain a point value of flux in units of mass per area-time (e.g. milligrams per square meter-second) for the identified location. These values may be plotted, the contoured areas obtained, and the mass flow rate obtained in mass per unit time.

A vertical mass flow rate of airborne matter may also be calculated by using the vertical component of wind velocity in conjunction with an essentially horizontal measurement surface.

Another calculation methodology would be to use the individual point (identified location) measurements of airborne matter to calculate an average concentration along a path of known length, thereby obtaining an average path-integrated concentration in volume per volume-length (e.g. parts per million-meters) or mass per length squared. In this case, maps in the physical sense need not be produced. However, this is equivalent to mapping the concentration measurements since each concentration measurement would have a geographic location and altitude value either estimated or attached to it, and the data would be a processed version of an airborne matter concentration map in one or more measurement surfaces through a cross-section or profile of the emission plume. The path-integrated concentration of each parallel or nearly-parallel horizontal or near horizontal path could then be used with a calculation methodology such as that described in U.S. Pat. No. 4,135,092 (which is incorporated herein by reference).

The software may comprise statements and instructions for mapping concentrations of airborne matter in an emission plume. The software may also comprise statements and instructions for obtaining a mass flow rate measurement or an emission discharge rate of airborne matter at a site, and correcting the measurements for the background concentration of airborne matter. The wind velocity, concentration measurements, identified location, distance of the apparatus above the ground surface, measurement path length, and the background concentration of airborne matter may be obtained as described herein. The resulting airborne concentration data, resulting mass flow rate measurement, or emission discharge rate may be stored on a computer readable memory for later access or manipulation. Alternatively, the mass flow rate and/or emission discharge rate can be calculated by hand.

Therefore, the present invention also provides for a method of mapping airborne concentrations of airborne matter in an emission plume, comprising:

a) measuring airborne matter at one or more than one identified locations using an optical sensing instrument (OSI) mounted on a vehicle operatively connected with one or more than one matter samplers mounted on the vehicle, by passing the one or more than one airborne matter samplers through an airspace to be sampled and obtaining one or more concentration measurements, a geographic position and an altitude value for each of the one or more identified locations; and b) mapping the concentration measurements relative to the geographic position and altitude values for each of the one or more identified locations to obtain an airborne matter concentration distribution map in one or more measurement surfaces through a cross-section or profile of the emission plume.

Additionally, the invention provides for a method for obtaining a mass discharge rate measurement of airborne matter at a site, comprising the steps of:

a) mounting the apparatus (OSI, matter sampler, location device, distance to ground surface measurement device) on a vehicle;

b) moving the vehicle-mounted matter sampler(s) transverse to a wind direction along one or more measurement paths, with sampling runs at different elevations, to form a measurement surface, and obtaining point concentration measurements and the location and distance to ground surface of each measurement with the apparatus;

c) mapping the concentration information obtained in two or three dimensions with respect to the ground surface to develop an airborne matter concentration map in the measurement surface through a cross-section or profile of the emission plume;

d) determining wind velocity at one or more locations and/or one or more heights above ground surface at or near each of the one or more than one measurement surface, to develop a wind speed distribution map in a plane perpendicular to the wind direction; and e) integrating the airborne matter concentration values with the appropriate wind velocity values to obtain the mass flow rate of airborne matter in mass per unit time.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way, including variations in the method of calculation to arrive at essentially the same mass flow rate result.

What is claimed is:

1. A method of producing an airborne matter concentration distribution map in an emission plume, comprising:

(a) measuring airborne matter at one or more than one identified locations using an optical sensing instrument (OSI) mounted on a vehicle operatively connected with one or more than one matter samplers mounted on the vehicle, by passing the one or more than one matter samplers through an airspace to be sampled and obtaining one or more concentration measurements, a geographic position and an altitude value for each of the one or more identified locations; and (b) mapping the concentration measurements relative to the geographic position and altitude values for each of the one or more identified locations to obtain the airborne matter concentration distribution map in one or more measurement surfaces through a cross-section or profile of the emission plume.

2. The method of claim 1 further comprising the steps of:

(c) determining a wind velocity for each identified location in the one or more measurement surfaces to obtain a wind velocity distribution map for each of the one or more measurement surfaces;

(d) integrating the airborne matter concentration value for each point in the one or more measurement surfaces with the wind velocity for each identified location in the one or more measurement surfaces to obtain the mass flow rate of airborne matter in mass per unit time.

3. The method of claim 1, further comprising a step of correcting for a background concentration of airborne matter or an upwind emission source by determining the background concentration of the airborne matter and subtracting this concentration from the measured concentration of airborne matter at the one or more than one identified locations.

4. The method of claim 1 wherein the airborne matter in step (a) is measured using an optical sensing method selected from: tunable diode laser (TDL) absorption spectroscopy, differential absorption laser detection and ranging (DIAL), open path Fourier transform infrared (OP-FTIR) spectroscopy, differential optical absorption spectroscopy (DOAS) or Raman spectroscopy.

5. The method of claim 1 wherein the one or more matter samplers includes a measurement cell comprising an air sample and a measurement beam.

6. The method of claim 1 wherein the OSI and matter samplers are integrated in a cavity ring-down spectrometer.

7. The method of claim 1, wherein the altitude value is determined using a laser range finder, a fixed measure, or an altimeter in conjunction with topographic information.

8. The method of claim 1 wherein the geographic position is determined using a global positioning system, radar, or one or more laser range-finders.

9. The method of claim 1 wherein the length of the one or more measurement surfaces spans the width of the emission plume.

10. The method of claim 1 wherein the height of the one or more measurement surfaces is about equal to, or greater than the height of the emission plume.

11. The method of claim 1 wherein the vehicle is an airplane, glider or helicopter.

12. The method of claim 1 wherein the vehicle is a ground-based land conveyance.

13. The method of claim 1 wherein the one or more matter samplers comprises a single pass cell.

14. The method of claim 1 wherein the one or more matter samplers comprises a multipass cell.

15. The method of claim 1 wherein an air sample inlet of the one or more matter samplers, is fixed to an external surface of the vehicle, or towed on a dragline.

16. The method of claim 1 wherein the vehicle passes through the airspace transverse to a wind direction.

17. The method of claim 1, wherein the point concentration measurements of airborne matter are averaged along one or more measurement paths of known length to obtain one or more average or path-integrated concentrations of the airborne matter.

18. The method of claim 2 wherein the wind velocity is obtained with an anemometer or sodar or by differential measurement of vehicle air velocity and vehicle ground velocity.

19. A computer readable memory having recorded thereon statements and instructions for execution by a computer to carry out the method of claim 1.

20. The method of claim 2, further comprising a step of correcting for a background concentration of airborne matter or an upwind emission source by determining the background concentration of the airborne matter and subtracting this concentration from the measured concentration of airborne matter at the one or more than one identified locations.

* * * * *